United States Patent
Fernández

(10) Patent No.: US 9,301,886 B2
(45) Date of Patent: Apr. 5, 2016

(54) REUSABLE SANITARY PAD

(76) Inventor: Dolores Rubio Fernández, Ann Arbor, MI (US)

( * ) Notice: Subject to any disclaimer, the term of this patent is extended or adjusted under 35 U.S.C. 154(b) by 523 days.

(21) Appl. No.: 13/584,411

(22) Filed: Aug. 13, 2012

(65) Prior Publication Data

US 2012/0310194 A1    Dec. 6, 2012

Related U.S. Application Data

(63) Continuation of application No. PCT/ES2011/000027, filed on Feb. 11, 2011.

(30) Foreign Application Priority Data

Feb. 11, 2010    (ES) .................... 201000166

(51) Int. Cl.
| A61F 13/15 | (2006.01) |
| A61F 13/20 | (2006.01) |
| A61F 13/49 | (2006.01) |
| A61F 13/56 | (2006.01) |
| A61F 13/78 | (2006.01) |
| A61L 15/40 | (2006.01) |

(52) U.S. Cl.
CPC ..... *A61F 13/49004* (2013.01); *A61F 13/15268* (2013.01); *A61F 13/5605* (2013.01); *A61F 13/78* (2013.01); *A61L 15/40* (2013.01)

(58) Field of Classification Search
USPC ............ 604/365, 367, 377–378, 383, 385.01, 604/385.15
See application file for complete search history.

(56) References Cited

U.S. PATENT DOCUMENTS

| 2006/0224136 A1 | 10/2006 | Martinez |
| 2009/0151105 A1 | 6/2009 | Bohannon et al. |
| 2009/0299313 A1 | 12/2009 | Knightingale et al. |
| 2010/0227138 A1* | 9/2010 | Ouellette .................. 428/219 |
| 2011/0092933 A1* | 4/2011 | Canales Espinosa de los Monteros et al. .......... 604/359 |
| 2011/0152814 A1* | 6/2011 | Seneviratne ................ 604/375 |

FOREIGN PATENT DOCUMENTS

| DE | 20 2004 015542 U1 | 12/2004 |
| DE | 20200401552 U1 | 12/2004 |
| EP | 2111833 A1 | 10/2009 |
| ES | 1049249 | 11/2001 |
| WO | 2009106899 A1 | 9/2009 |

OTHER PUBLICATIONS

International Search Report mailed Jun. 15, 2011 for PCT App. No. PCT/ES2011/000027.

(Continued)

*Primary Examiner* — Michele M Kidwell
(74) *Attorney, Agent, or Firm* — Burris Law, PLLC

(57) ABSTRACT

A reusable pad, such as those intended for protection during menstrual periods, is provided that includes an inner layer made of two layers of natural cellulose fabric, the layers of natural cellulose fiber bonded together by a biodegradable polyurethane film. Two intermediate layers of absorbent organic bamboo fabric are also provided, along with an outer cover formed by a fabric made from cotton. The inner layer is inserted between the two intermediate layers to form a composite, and the composite is inserted into the outer cover.

16 Claims, 4 Drawing Sheets

(56) References Cited

OTHER PUBLICATIONS

Wikipedia, the free encyclopedia. Diaper. Feb. 12, 2009. [Retrieved Jan. 13, 2014 from http://en.wikipedia.org/wiki/Diaper ]. See first paragraph of paragraph "Cloth".

Fehrenbacher, J. GDiapers: We Review the Planet's First Flushable Diaper. Sep. 16, 2008. [Retrieved May 6, 2013 from http://www.inhabitots.com/gdiapers-we-review-the-planets-first-flushable-diaper ]. See paragraphs 1 and 3.

European Search Report for European Patent Application No. 11741927.5 mailed on Feb. 26, 2014.

* cited by examiner

REUSABLE SANITARY PAD

CROSS-REFERENCE TO RELATED APPLICATIONS

This application is a continuation of International Application No. PCT/ES2011/000027, filed on Feb. 11, 2011, which claims the benefit of P201000166, filed on Feb. 11, 2010. The disclosures of the above applications are incorporated herein by reference.

FIELD

The disclosure relates to sanitary pads used by women during their menstrual period. A pad made with such structural characteristics as to make it reusable, and which offers organic conditions that are very advantageous for the function for which it is intended, is being proposed.

BACKGROUND

Currently, the use of means of containment is generalized among women during their menstrual period. Sanitary pads are the most utilized means for this purpose due to their external.

There are sanitary pads with diverse structural shapes available, meant to conceal the physiological function of the application use in the most adequate manner, combining this factor with others, such as comfort of use, economy, and hygiene.

In this sense, the pads are conventionally made with materials that are physiologically adequate for contact with the body and capable of providing absorption and impermeability by using mostly synthetic materials with said qualities.

Pads made this way are generally used and discarded, that is, disposable, after only one use, which carries with it significant inconveniences with regard to the economic cost for the users and pad disposal represents a burden of contaminating waste, since a normal women utilizes on average about 17,000 pads during her fertile years.

Reusable pads have been developed in order to palliate the problems derived from the use of large quantities of pads, but presently, these types of pads are made with an inner layer of textile material, whose composition is usually 100% acetate, viscose or rayon, or nylon, polyester or polyurethane, which does not provide a completely effective impermeability.

On the other hand, the single-use pads that are currently widely used also tend to be made with chemical products, such as chlorine and perfumes, and products derived from petroleum, such as plastics and adhesives, which cause on many occasions continuous discomfort and allergies to the persons that use them (women, patients, or disabled persons).

According to the present disclosure, a pad made of an inner layer of 100% cellulose fiber, whose characteristics cause the pad to perform much better than those known until now, is being proposed.

The pad includes an inner layer made of two layers of fabric of natural cellulose bonded to a polyurethane film inserted between them, with said inner layer being inserted between two or more layers of absorbent fabric made from organic bamboo. All of which is arranged within a cover made from conventional and organic cotton fabric.

This way, a less thick pad is obtained, whose structural composite provides optimal characteristics in regard to impermeability, breathability and absorbency, as well as hygienic qualities that prevent problems related to infections and/or irritations caused by contact with plastics, chlorine, perfume or other petrochemical products utilized in conventional pads.

The materials from which the pad is made provide it with great softness and make it optimal for use by persons with sensitive skin. It prevents irritations and controls temperature because of its nanostructure, which allows moisture absorption with extraordinary ease. And from a hygienic point of view, cellulose fiber provides antibacterial properties, while the organic bamboo provides an antimicrobial capacity.

The bonding of the natural cellulose fabric layers and the polyurethane film on the inner layer is attained by means of a nano-stitch system, which makes this layer especially thin, which ensures the pad's optimal performance. The polyurethane is biodegradable and does not contain any substances that may be toxic or harmful to the human body.

In addition, the natural materials with which this new pad is made, are completely biodegradable. This eliminates the impact on environmental pollution caused by the disposal of discarded pads.

The possibility of reusing the pad by washing it also allows a drastic reduction of the number of pads that are needed. One same pad can be used for a long time and, for this reason, the number of pads women must use during their fertile years is very small. This implies a significant cost reduction when compared to the use of conventional disposable pads as well as considerable less trouble associated with having to purchase the pads and having the pads available when needed.

Because of this, the new sanitary pad offers very advantageous characteristics when compared to the conventional pads currently on the market. This puts it in a class of its own and gives it preferential characteristics for the application function it is destined for.

DRAWINGS

DETAILED DESCRIPTION

Figure 1:
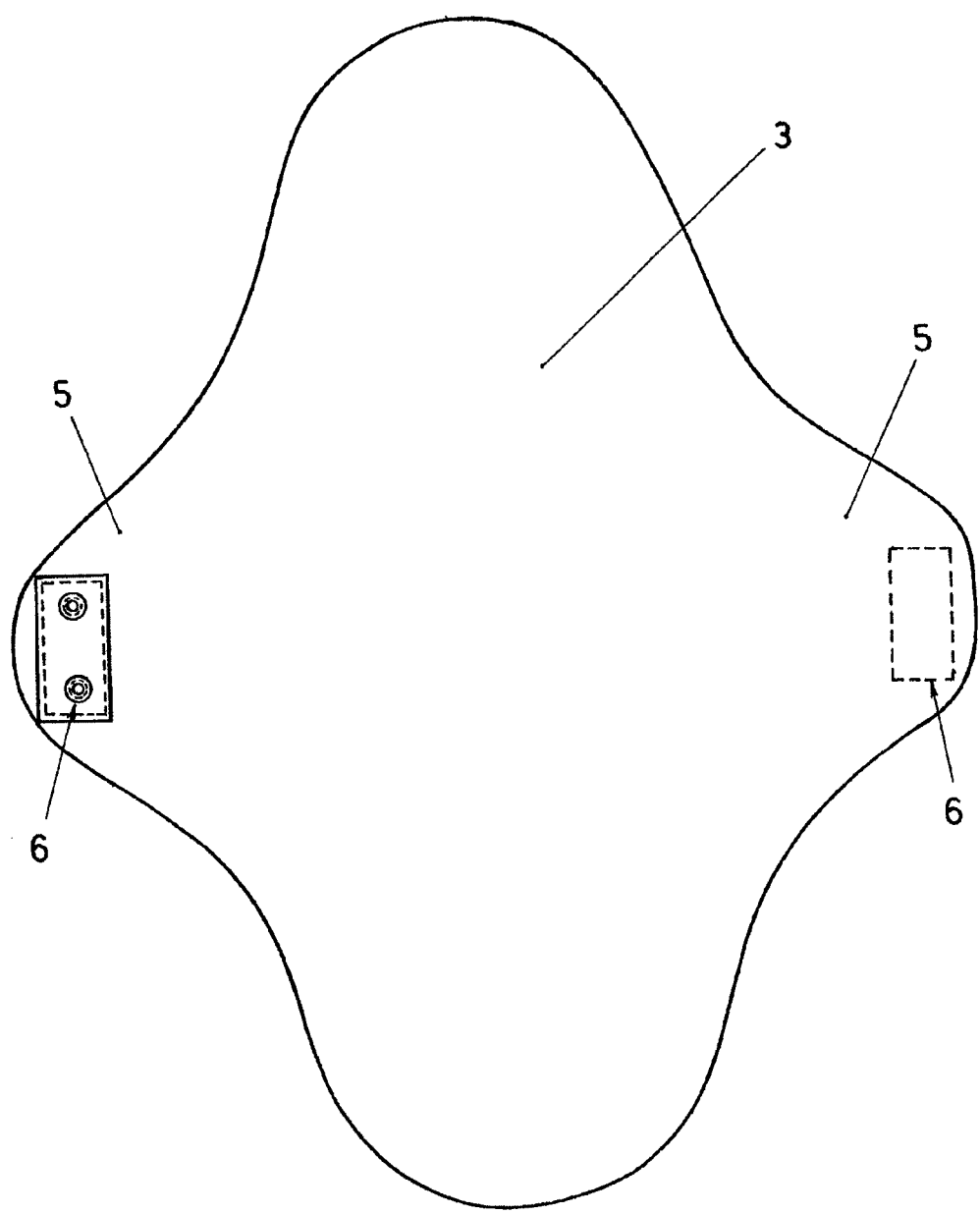
FIG. 1 shows an example of the making of the preferred pad viewed from the side that comes in contact with the user.
Figure 2:
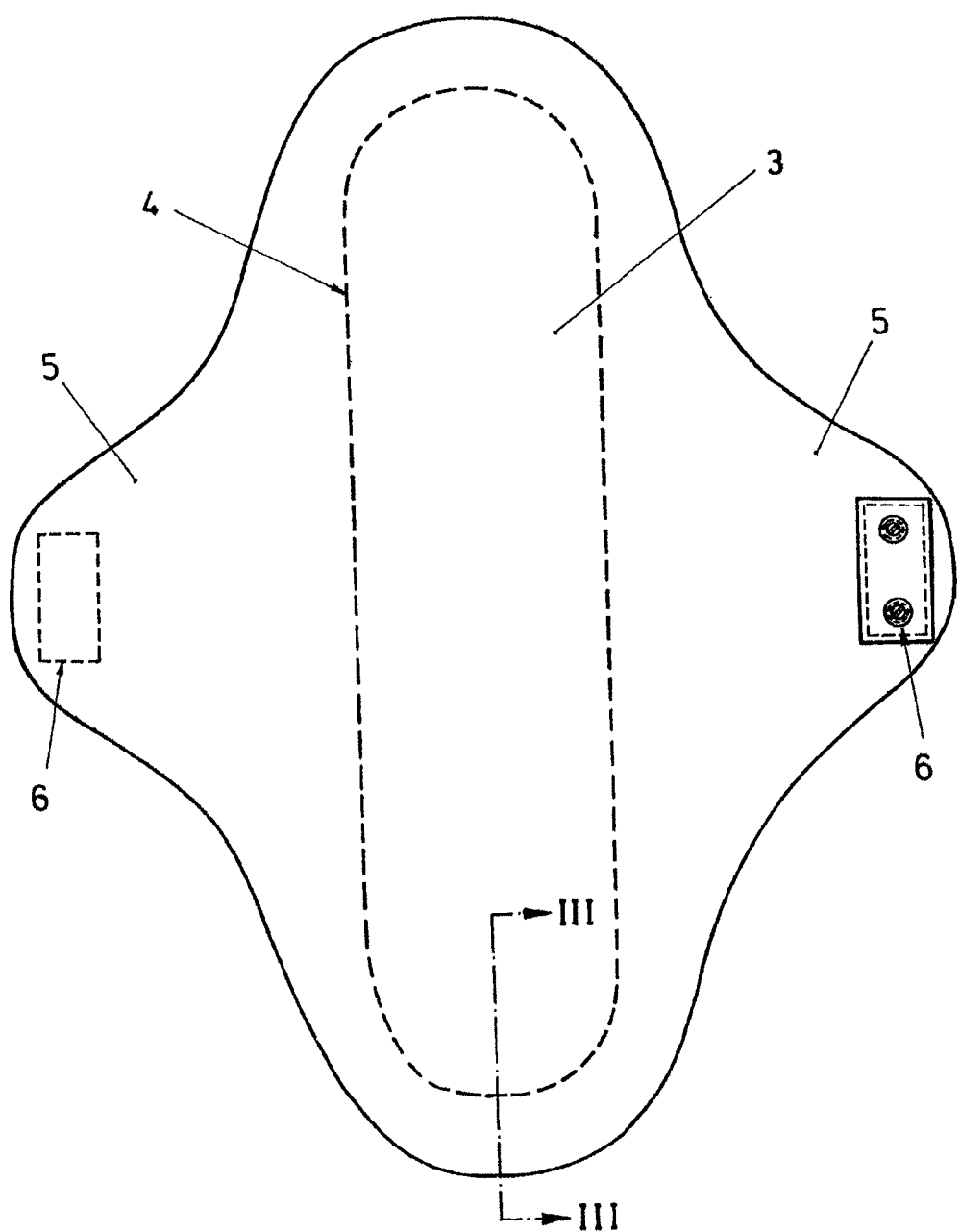
FIG. 2 shows a view of the rear side of the same pad.
Figure 3:
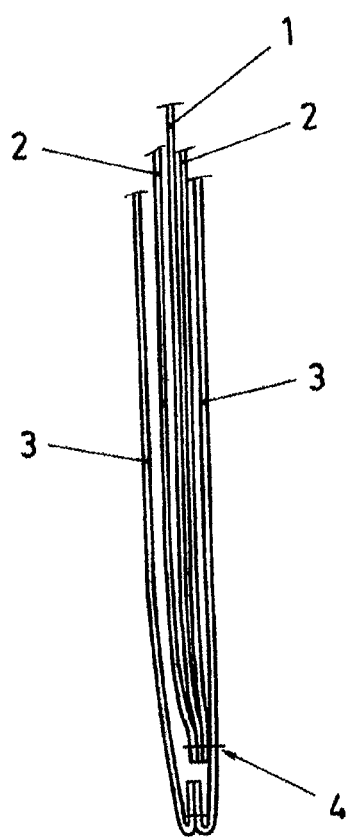
FIG. 3 shows an enlarged detail from section III-III shown in the previous picture.

The present disclosure relates to a sanitary pad for women's menstrual periods that has a structural configuration that provides optimal characteristics for the function for which it is used and the possibility of reutilization.

Said pad is made of a structural composite that comprises an inner layer (1) made of two layers of natural cellulose fabric. Said natural cellulose fabric layers are bonded to a polyurethane film that is inserted between them, which causes the composite to become impermeable.

This inner layer (1) is inserted between intermediate layers (2) made from absorbent organic bamboo fabric, where two or more of these intermediate layers (2) can be provided according to the desired absorptive capacity of the pad.

The composite of said layers (1 and 2) is inserted into an outer cover (3) made of conventional cotton or organic cotton fabric, through which the outer surface and the shape of the pad are determined.

This is how an impermeable, breathable and absorbent pad is obtained, which has a structural composite formed in its entirety by natural materials. This offers optimal organic properties for hygienic use, and it also results in that said structural composite is biodegradable and consequently, has no contaminating repercussions when the pads are disposed of. The pad's structural composition makes it washable, and therefore, reusable. So the same pad may be used repeatedly for a long time, thus avoiding the problems and inconveniences related to conventional single-use pads.

The inner composite formed by the inner layer (1) and the intermediate layers (2) is held inside the outer cover (3) with stiches (4) for its immobilization. Said seam (4) is only present over the outer cover part (3) that corresponds to the back of the pad, that is, the part opposite to the side that comes in contact with the user.

In this way, the pad is provided with a completely even face on the part that comes in contact with the user, to avoid threads from the stiches (4) which attach the inner composite, or the roughness that said stiches (4) may cause, and so they won't create friction points that may cause discomfort for the user of the pad.

Figure 4:
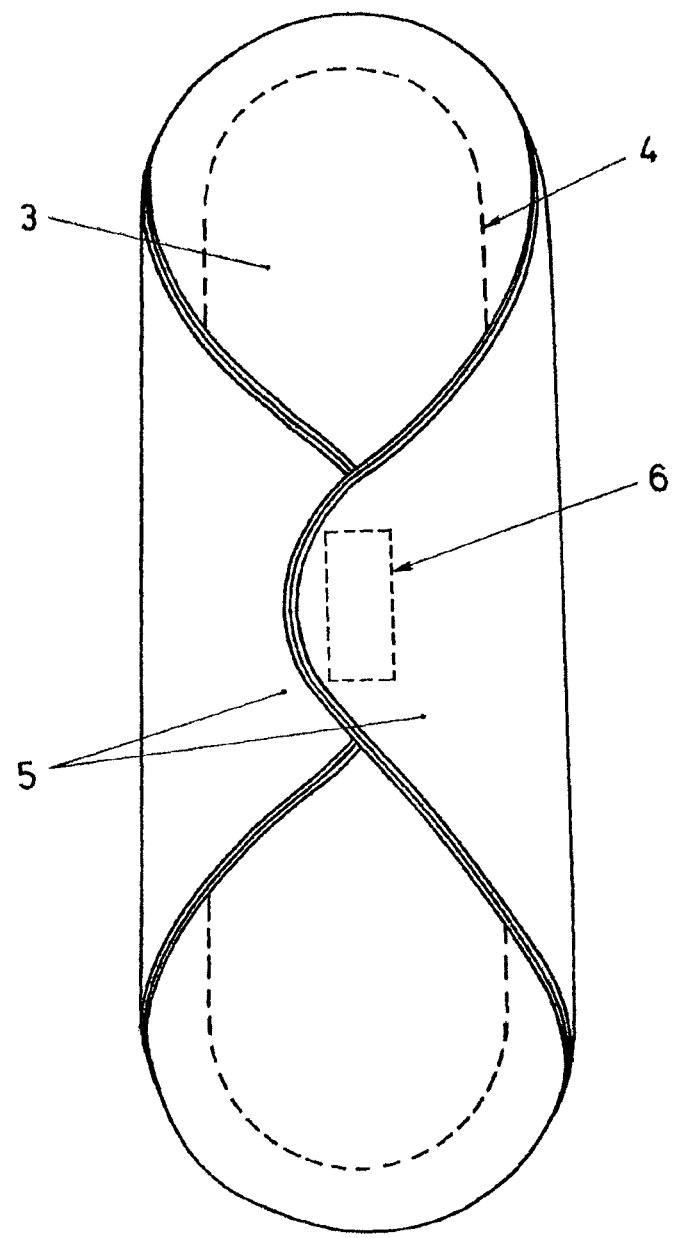
FIG. 4 shows a view of the pad folded in a fixed position for use on the user's undergarment.

The pad may assume different shapes and sizes with regard to its configuration, without this altering the concept of the structural shape, with which the invention is concerned. For example, it is possible to adopt a conventional configuration with side wings (5) and possibly attachment means (6) between them, to keep the pad together by means of buttons, such as the one shown in FIG. 4, on an undergarment of the user, without this implementation being restrictive.

It should be noted that even though the preferred application of the preferred pad is for feminine use during menstrual periods, this does not exclude its use for other applications, such as the use by persons suffering from any degree of incontinence, as well as for people who are ill or disabled.

While preserving the same structural distribution of the pad, it is provided that the materials of the component layers can be arranged in different order, for example, with the intermediate cotton layers (2) and the outer cotton cover (3) on one side and the organic bamboo fabric on the other side.

What is claimed is:

1. A reusable sanitary pad consisting of biodegradable materials, the reusable sanitary pad comprising:
    an inner layer made of two layers of natural cellulose fabric, said layers of natural cellulose fiber bonded together by a biodegradable polyurethane film;
    two intermediate layers of absorbent organic bamboo fabric; and
    an outer cover formed by a fabric made from cotton,
    wherein the inner layer is disposed between the two intermediate layers to form a composite, the composite being held inside the outer cover.

2. The reusable sanitary pad according to claim 1, wherein the two intermediate layers of absorbent organic bamboo fabric define characteristics according to an absorptive capacity desired.

3. The reusable sanitary pad according to claim 1, wherein the inner layer and the intermediate layers are secured to the outer cover by stitches that extend through only a back of the reusable sanitary pad.

4. The reusable sanitary pad according to claim 1 defining a shape having side wings extending from a central portion.

5. The reusable sanitary pad according to claim 4 further comprising attachment means secured to outer portions of the side wings, the attachment means adapted to secure the reusable sanitary pad to an undergarment of a user.

6. The reusable sanitary pad according to claim 1, wherein the outer cover is made from an organic cotton.

7. A reusable sanitary pad consisting of biodegradable materials, the reusable sanitary pad comprising:
    an inner layer made of two layers of natural cellulose fabric, said layers of natural cellulose fiber bonded together by a biodegradable polyurethane film;
    two intermediate layers of absorbent organic bamboo fabric disposed on one side of the inner layer; and
    an outer cover formed by a fabric made from cotton disposed on an opposite side of the inner layer.

8. The reusable sanitary pad according to claim 7, wherein the two intermediate layers of absorbent organic bamboo fabric define characteristics according to an absorptive capacity desired.

9. The reusable sanitary pad according to claim 7, wherein the inner layer is secured to the outer cover by stitches that extend through only a back of the reusable sanitary pad.

10. The reusable sanitary pad according to claim 7 defining a shape having side wings extending from a central portion.

11. The reusable sanitary pad according to claim 10 further comprising attachment means secured to outer portions of the side wings, the attachment means adapted to secure the reusable sanitary pad to an undergarment of a user.

12. The product sanitary pad according to claim 7, wherein the outer cover is made from an organic cotton.

13. A reusable sanitary pad consisting of biodegradable materials, the reusable sanitary pad comprising:
    an inner layer made of two layers of natural cellulose fabric, said layers of natural cellulose fiber bonded together by a biodegradable polyurethane film;
    two intermediate layers of absorbent organic bamboo fabric; and
    an outer cover formed by a fabric made from cotton,
    wherein the inner layer is disposed between the two intermediate layers to form a composite, the composite being held inside the outer cover, the reusable sanitary pad defining a shape having side wings extending from a central portion.

14. The reusable sanitary pad according to claim 13 further comprising attachment means secured to outer portions of the side wings, the attachment means adapted to secure the reusable sanitary pad to an undergarment of a user.

15. The reusable sanitary pad according to claim 13 wherein the inner layer and the intermediate layers are secured to the outer cover by stitches that extend through only a back of the reusable sanitary pad.

16. The reusable sanitary pad according to claim 13, wherein the two intermediate layers of absorbent organic bamboo fabric define characteristics according to an absorptive capacity desired.

* * * * *